US006632678B2

(12) United States Patent
Aiken et al.

(10) Patent No.: US 6,632,678 B2
(45) Date of Patent: Oct. 14, 2003

(54) METHOD FOR PERFORMING ACTIVATED CLOTTING TIME TEST WITH REDUCED SENSITIVITY TO THE PRESENCE OF APROTININ AND FOR ASSESSING APROTININ SENSITIVITY (75) Inventors: Jennifer C. Aiken, Wheat Ridge, CO (US); Jon H. Henderson, Wheat Ridge, CO (US); Barbara A. DeBiase, Wheat Ridge, CO (US)

(73) Assignee: Sienco, Inc., Wheat Ridge, CO (US)

(*) Notice: Subject to any disclaimer, the term of this patent is extended or adjusted under 35 U.S.C. 154(b) by 442 days.

(21) Appl. No.: 09/753,974

(22) Filed: Jan. 3, 2001

(65) Prior Publication Data

US 2002/0127730 A1 Sep. 12, 2002

(51) Int. Cl.$^7$ .............................................. G01N 33/86
(52) U.S. Cl. ........................ 436/69; 600/369; 73/64.41; 702/19
(58) Field of Search ........................ 436/63, 69; 435/2, 435/13; 702/19; 600/369; 73/64.41

(56) References Cited

U.S. PATENT DOCUMENTS

| | | | |
|---|---|---|---|
| 3,395,210 A | | 7/1968 | Lenahan et al. ................ 424/2 |
| 3,492,096 A | | 1/1970 | Hattersley ..................... 23/230 |
| 4,189,382 A | * | 2/1980 | Zine, Jr. ....................... 210/714 |
| 4,426,290 A | * | 1/1984 | Ichikawa et al. ............ 210/516 |
| 4,579,828 A | * | 4/1986 | Ali ............................... 501/12 |
| 4,770,779 A | * | 9/1988 | Ichikawa et al. ............ 210/516 |
| 4,985,026 A | * | 1/1991 | Kasai et al. ................. 604/403 |
| 5,016,469 A | | 5/1991 | Henderson ................... 73/64.1 |
| 5,091,304 A | * | 2/1992 | La Duca et al. .............. 435/13 |
| 5,138,872 A | | 8/1992 | Henderson ................. 73/64.41 |
| 5,314,826 A | | 5/1994 | Baugh .......................... 436/69 |
| 5,413,786 A | * | 5/1995 | Anraku ....................... 514/185 |
| 5,506,146 A | | 4/1996 | Josef ............................ 436/69 |
| 5,599,683 A | | 2/1997 | Nishikawa et al. ............ 435/13 |
| 5,628,961 A | | 5/1997 | Davis et al. ................... 422/63 |
| 5,629,209 A | | 5/1997 | Braun, Sr. et al. ............ 436/69 |
| 5,648,228 A | | 7/1997 | Nishikawa et al. ............ 435/13 |
| 5,705,395 A | | 1/1998 | Griffin et al. ................. 436/69 |
| 5,888,824 A | * | 3/1999 | Isogawa et al. ............... 436/18 |
| 5,895,842 A | | 4/1999 | Henderson ................. 73/54.26 |

OTHER PUBLICATIONS

J.S. Wang et al., "Monitoring of Heparin–induced Anticoagulation with Kaolin–activated Clotting Time in Cardiac Surgical Patients Treated with Aprotinin," Anesthesiology, vol. 77, No. 6, Dec., 1992 (pp. 1080–1084).

J.S. Wang et al., "In Vitro effects of aprotinin on activated clotting time measured with different activators," Journal of Thoracic and Cardiovascular Surgery, vol. 104, No. 4, Oct., 1992 (pp1135–40).

W. Dietrich et al., "Influence of High–dose Aprotinin on Anticoagulation, Heparin Requirement, and Celite–and Kaolin–Activated clotting Time in Heparin–pretreated patients undergoing Open–Heart Surgery," Anesthiology, vol. 83, No. 4, Oct., 1995 (pp. 679–689).

W. Dietrich et al., "Effect of celite and kaolin on activated clotting time in the presence of aprotinin: Activated Clotting time is reduced by binding of aprotinin to kaolin," Journal of Thoracic and Cardiovascular Surgery, vol. 109, No. 1, Jan., 1995 (pp. 177–178.

* cited by examiner

*Primary Examiner*—Maureen M. Wallenhorst
(74) *Attorney, Agent, or Firm*—William E. Hein (57) ABSTRACT A coagulation test for determining the activated clotting time (ACT) of blood in the presence of heparin that produces test results that are substantially insensitive to the drug aprotinin. The activator is formulated to be a combination of celite and bentonite. The ACT results obtained with this formulation are similar to celite ACT tests on heparinized blood while simultaneously being unaffected by aprotinin. Additionally, a method for quantifying the aprotinin effect of different ACT formulations is disclosed.

11 Claims, 10 Drawing Sheets

METHOD FOR PERFORMING ACTIVATED CLOTTING TIME TEST WITH REDUCED SENSITIVITY TO THE PRESENCE OF APROTININ AND FOR ASSESSING APROTININ SENSITIVITY

BACKGROUND AND SUMMARY OF THE INVENTION

This invention relates to the determination of the activated clotting time (ACT) of blood or plasma, specifically for patients receiving the drugs heparin and aprotinin.

Heparin is an anticoagulant drug used during surgeries requiring the use of extracorporial circuits, such as cardiopulmonary bypass (CPB). Heparin prevents blood clots from forming while blood is flowing through the circuit. In order to ensure sufficient anticoagulation, doctors must be able to measure heparin's anticoagulant effect on blood. The anticoagulant effect of heparin is often managed using the activated clotting time (ACT) as determined by in vitro diagnostic tests. The ACT is prolonged after heparin administration. For example, without heparin, the ACT is generally about 120 seconds, while the ACT after heparin administration is typically beyond 480 seconds. An ACT of greater than 480 seconds is considered by many clinicians to be the minimum amount of heparin anticoagulation effect necessary for CPB surgery. The object of an ACT test is to indicate if adequate heparin has been administered to the patient in order to proceed with the surgical procedure without risk of forming blood clots.

Heparin is metabolized during surgery. Consequently, heparin must be administered both before and during CPB surgery in order to maintain a sufficient level of anticoagulation. Also, the anticoagulant effect of heparin varies from patient to patient. Therefore, different patients require different amounts of heparin, both before and during CPB surgery.

Several different tests are used throughout the world to manage heparin administration during CPB surgery. The most widely used tests for heparin management are the ACT, activated partial thromboplastin time (aPPT), and protamine titration of heparin. Of these tests, ACTs are the most common, least expensive, and most convenient way to manage heparin administration during a CPB surgical procedure. Heparin management protocols vary among medical institutions, but typically, when the ACT drops below a threshold time of typically 400 to 480 seconds, additional heparin is administered. ACT tests contain a contact activator to trigger clot formation. The two activators currently in general used for CPB surgery are diatomaceous earth (celite) and kaolin, a type of clay. Glass beads (silicon dioxide) are also used as a contact activator for ACT tests, although they are typically not used in CPB surgery because glass beads provide less contact activation than comparable amounts of celite or kaolin.

Several prior art instruments measure ACTs. Exemplary of these products are the Hemochron® 801 and Hemochron Jr. manufactured by International Technidyne Corporation, the Automated Coagulation Timer II and the Hepcon® Hemostasis Management System manufactured by Metronic HemoTec Inc., the Hemotec ACT manufactured by HemoTec, Inc., the Actalyke® manufactured by Array Medical, and the Sonoclot® Coagulation & Platelet Function Analyzer manufactured by Sienco, Inc. All of these instruments measure the time required to form a clot. Measurement time typically begins when the whole blood sample is mixed with an activator and ends when a clot is detected.

Aprotinin, manufactured under the name Trasylol® by Bayer Corporation, is a drug that has been shown to reduce blood loss after cardiopulmonary bypass (CPB) surey. Researchers do not completely understand the process or processes by which aprotinin achieves this reduction in bleeding. Aprotinin is a protease inhibitor neutralizing primarily plasmin and kallikrein. It also reduces glycoprotein loss in platelets, thereby preserving the platelets' ability to aggregate after CPB. The net effects of aprotinin administration reduce the need for post-operative blood transfusions and re-exploratory surgery to stop bleeding. Aprotinin may have additional effects on hemostasis via other mechanisms.

An undesirable and potentially dangerous side effect of aprotinin is that it prolongs celite activated ACT results in the presence of heparin. For example, a celite ACT on a heparinized patient may be 480 seconds. The same patient with the same amount of heparin plus aprotinin may have an ACT substantially over 700 seconds. The celite ACT result is not a useful measurement for the heparin anticoagulant effect in the presence of aprotinin because the aprotinin prolongs the ACT result. Managing heparin with celite ACT tests is not effective because, in the presence of aprotinin, the ACT is substantially delayed, creating a risk of under heparinization and subsequent clotting during surgery. Also, any time wasted waiting for a 700-second ACT is a significant operating room cost and should be avoided when possible.

Kaolin activated ACTs have been investigated as a preferred alternative to celite activated ACTs for use with patients receiving both heparin and aprotinin. Numerous publications state that kaolin ACTs are not prolonged by aprotinin. These publications include J. S. Wang et al., "Monitoring of Heparin-induced Anticoagulation with Kaolin-activated Clotting Time in Cardiac Surgical Patients Treated with Aprotinin," Anesthesiology, 77:1080–1084, December 1992, and W. Dietrich et al., "Influence of Hi-dose Aprotinin on Anticoagulation, Heparin Requirement, and Celite and Kaolin Activated Clotting Time in Heparin-pretreated Patients Undergoing Open-Heart Surgery," Anesthesiology, 88: 679–689, October 1995. The published research of kaolin activated ACTs appears to have been based on the assumption that all kaolin reagents perform similarly when used for ACTs. Each of these published studies investigated commercially available kaolin ACTs or custom kaolin ACTs using only one type of kaolin. The idea that the source or purity of kaolin may contribute to the stability of kaolin ACT results in the presence of heparin is never discussed.

The original development objective of the present inventors was to develop a kaolin ACT for use with the Sonoclot Analyzer in applications using aprotinin during CPB surgery. Based on published information, the initial assumption was that this development effort would be straightforward. The first kaolin formulations used USP grade kaolin, part number 5645 from Mallinckrodt Chemical, Inc., Kentucky, in a concentration that produced a desired heparin dose response to other commercial kaolin ACT tests. When this formulation was tested for aprotinin stability, an unexpected result was found; this kaolin ACT was found to perform similar to celite ACTs rather than published performance for kaolin ACTs. The ACT results were significantly prolonged by aprotinin when heparin was also present. Subsequent work by the present inventors showed that kaolin activated ACT tests are highly dependent on the source and purity of kaolin.

This research also exposed another unexpected concern; any alteration of kaolin ACT results due to aprotinin is highly patient variable. Using kaolin from ACT tests manufactured by International Technodyne, it was found that the ACT results on heparinized blood were unaffected by aprotinin for most samples. However, in approximately 10% of blood samples taken from the normal population, the ACT results on heparinized blood were substantially prolonged by aprotinin. This is a significant concern because the patients with heparinized blood samples that produce prolonged ACT results in the presence of aprotinin may receive significantly less heparin. These patients are at risk for under heparinization and subsequent clotting of the CPB circuit. Published performance data on kaolin ACTs reported only sample mean and standard deviations; this statistical analysis can miss individual patient variability that occurs only in a small percentage of the sample population. Kaolin ACT performance in the presence of aprotinin is described in more detail hereinafter.

The manufacturer of aprotinin recognizes that aprotinin may compromise ACT based heparin management. The aprotinin product insert recommends minimum ACTs while on CPB of 750 or 480 seconds for celite or kaolin ACTs, respectively. The aprotinin product insert also states that heparin may be monitored by either of two alternative ways separate from ACT testing. The first alternative method is to administer heparin on a fixed-dose regimen based on the patient's weight and the duration of CPB, which is an older and less exact method for heparin management. The second alternative method is to measure the heparin level using a protamine titration. Neither of these methods is as easy, reliable, and convenient as measuring the ACT. In addition, the protamine titration method can increase the cost of the procedure by about $150.

In addition, measuring the level of heparin present in the blood is not as accurate an assessment of a patient's anticoagulation state as measuring the ACT. Heparin is an indirect anticoagulant and is effective only through bonding with antithrombin, also called antithrombin III, a natural anticoagulant present in blood. Heparin bonded to antithrombin is a much stronger anticoagulant than antithrombin alone. Certain patients are insensitive or resistant to heparin because they have low levels of antithrombin. Therefore, simply measuring the level of heparin is not sufficient to determine the effective anticoagulative state of the patient. An ACT test, however, determines the overall anticoagulation state of the blood and can be useful in managing heparin anticoagulation therapy.

Array Medical manufactures an ACT test termed MAX-ACT that uses a mixture of standard materials, including kaolin, celite, and glass beads. This formulation is intended to maximize factor XII activation. This formulation was investigated and was found to perform substantially equivalent to commercially available kaolin ACT formulations.

An ideal ACT test should have a dose response relationship solely influenced by heparin. Higher ACT results should indicate higher concentrations of circulating heparin. The absence or presence of aprotinin should not alter the ACT result. Current ACT formulations fall short of ideal ACT performance when aprotinin is used. For patients receiving both heparin and aprotinin, heparin prolongs the ACT result, and aprotinin may further prolong the test result. Consequently, in the presence of aprotinin, current ACT test results do not indicate the level of heparin anticoagulant effect and may expose the patient to a risk of inadequate and unsafe heparin administration. Celite tests are significantly prolonged by a combination of aprotinin and heparin in comparison to heparin alone. Kaolin ACT tests perform inconsistently in the presence of aprotinin. Some kaolin formulations perform similarly to celite ACT tests, and results are consistently prolonged in the presence of aprotinin and heparin in comparison to heparin alone. Other kaolin-activated ACT tests, including the kaolin used by International Technidyne Corporation, produce inconsistent results in the presence of both heparin and aprotinin. In most blood samples, the aprotinin has little effect on the ACT, while in others the ACT is substantially prolonged by aprotinin. With the kaolin ACT formulation used by International Technidyne Corporation, a prolonged ACT test result, for a blood sample that happens to be insensitive to aprotinin using this test formulation, would be due exclusively to the heparin, while in another blood sample that is sensitive to aprotinin, the ACT test result may be prolonged due to the combined effects of both the heparin and the aprotinin. Consequently, currently manufactured kaolin ACT test results are highly inaccurate in measuring the heparin anticoagulation effect for individual patients that show strong sensitivity to aprotinin in the presence of heparin when using a kaolin ACT. An ACT formulation that is less affected by aprotinin for a larger percentage of patients will improve anticoagulant safety in CPB surgery.

It would therefore be advantageous to provide an improved activated clotting time formulation that provides consistent response to the anticoagulant heparin regardless of the absence or presence of the drug aprotinin and a method for quantifying the aprotinin sensitivity of different activation formulations to evaluate aprotinin sensitivity performance.

One feature of the present invention is the provision of an in vitro diagnostic test useful for characterizing the anticoagulation effect of heparin that is not altered by the drug aprotinin.

Another feature of the present invention is the provision of an in vitro diagnostic test that also produces test results similar to current widely used tests for characterizing the anticoagulation effect of heparin.

Another feature of the present invention is the provision of an in vitro diagnostic test that further provides consistently equivalent results in the presence of heparin regardless of the absence or presence of aprotinin for a wide range of individuals rather than just average equivalence for a sample population.

Yet another feature of the present invention is the provision of a method to evaluate the performance of different activation formulations for an in vitro diagnostic test that is to be used to characterize the anticoagulation effect of heparin in the presence or absence of aprotinin that accounts for both average performance for a sample population and individual patient variability to different activation formulations so that accurate heparin anticoagulation management can be achieved for a large percentage of individual patients.

DETAILED DESCRIPTION OF THE INVENTION

Figure 2:
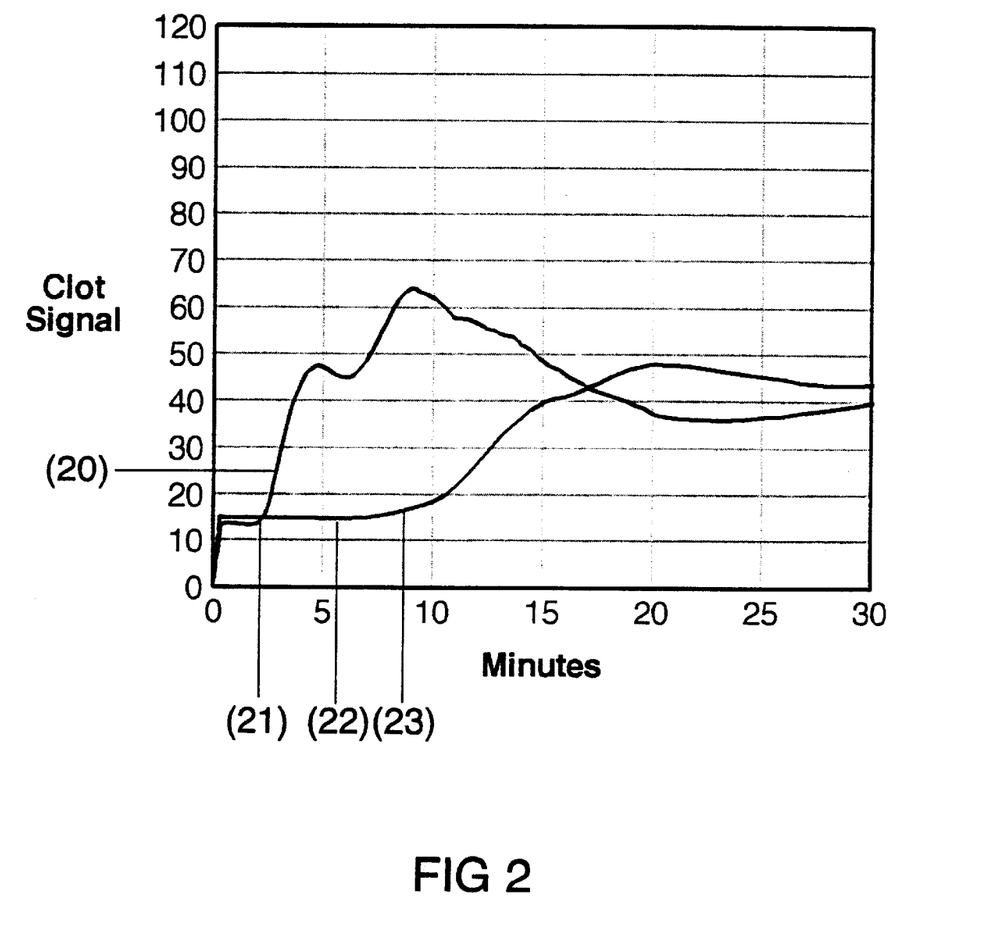
FIG. 2 shows ACT signatures obtained from celite activation run on whole blood and heparinized whole blood.

The present invention is directed toward an in vitro diagnostic test formulation that shows reduced sensitivity to the presence of aprotinin in heparinized blood samples. The test requires a blood sample container, a contact activation material, an optional mixing apparatus, such as a stir bar, and a means to detect the resulting blood clot. During the development of this invention, a prior art Sonoclot Coagulation & Platelet Function Analyzer manufactured by Sienco, Inc., Morrison, Colo., and described in U.S. Pat. Nos. 5,016,469, 5,138,872, and 5,895,842, was used to monitor the clot formation process and automate the measurement of the ACT result. The Sonoclot Analyzer provides an ACT result and also produces a graph that monitors the changes in viscosity that occur throughout the clot formation process, as illustrated in FIG. 2. This product is useful for research applications because it provides information on the entire clot formation process and requires a small amount of blood per test. Clotting studies were run using citrated whole blood samples obtained from multiple normal subjects using collection tubes (part number 366415) supplied by Becton Dickinson, Franklin Lakes, N.J., 0.330 µL of citrated whole blood, 0.017 µL 0.25 M $CaCl_2$, heparin, and the activation formulation were used for each ACT test. Blood samples were warmed to 37° C. immediately prior to testing. The amount of heparin was adjusted to achieve a control ACT between 300 to 600 seconds.

Figure 1:
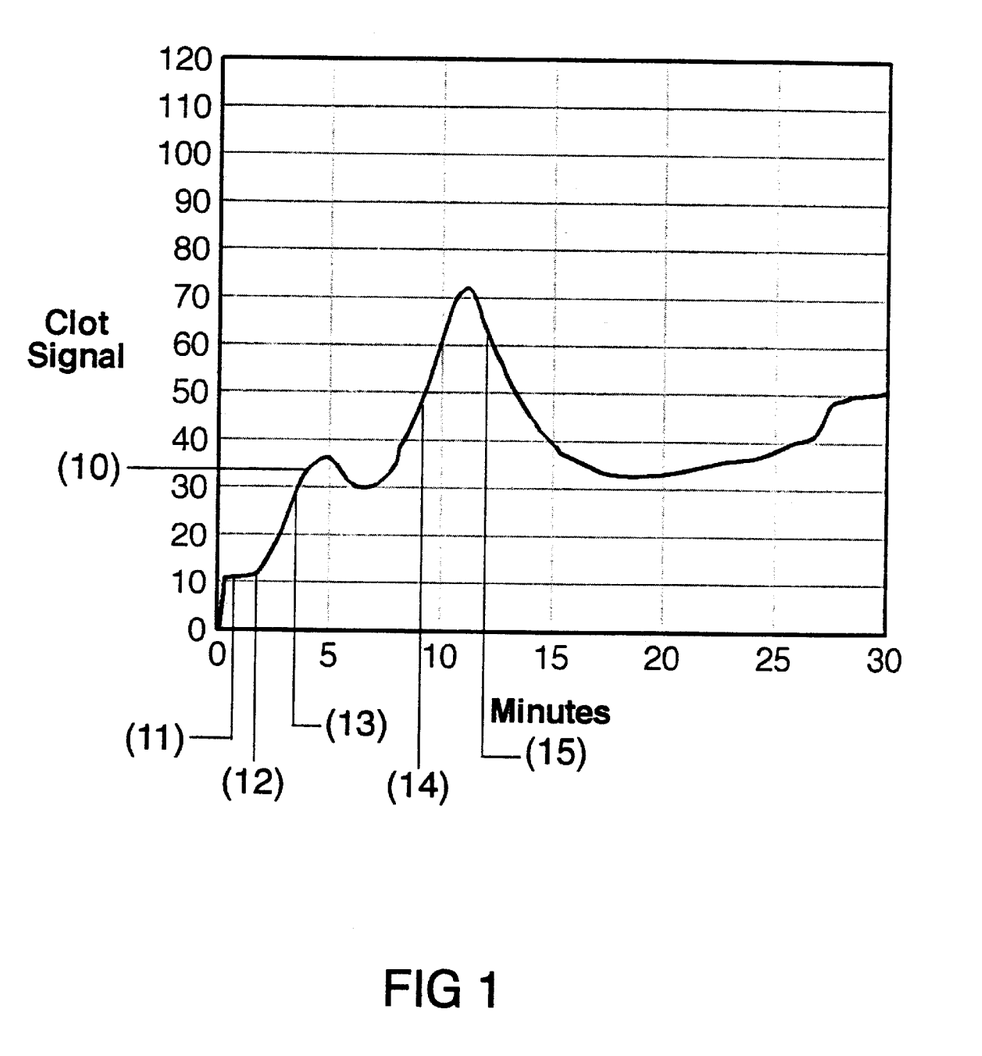
FIG. 1 shows an ACT signature obtained from celite activation run on whole blood.

FIG. 1 shows an ACT signature resulting from a clot formation test run on a Sonoclot Analyzer. This test produces typical graph 10, which is hereinafter referred to as a Sonoclot Signature. The Sonoclot Signature graphs the viscosity measurement of the Sonoclot Analyzer on the y-axis versus time on the x-axis. The viscosity measurement is in units of Clot Signals, which is a monotonic viscosity scale normalized to typical values obtained for blood samples. The time measurement is plotted in units of minutes. Each typical Sonoclot Signature has separate phases that correspond to different phases of hemostasis development. A liquid phase 11 is the relatively flat portion of the Sonoclot Signature located at the beginning thereof. When a clot begins to form, the Sonoclot Signature begins to increase in value at point 12 thereof. The time when the clot begins to form is the ACT, which is typically reported in seconds. Region 13 corresponds to the phase when the fibrinogen in the blood sample converts into a fibrin gel. Later in the Sonoclot Signature, as illustrated by regions 14 and 15, its shape may show phases of further changes in the viscosity measurement typically due to the effects of platelets modifying the fibrin gel into a mature clot. The phases related to the effects of platelets may cause the Sonoclot Signature to either rise, as in region 14, or fall, as in region 15.

FIG. 2 shows two Sonoclot Signatures 20, 22. Sonoclot Signature 20 results from a typical sample without any heparin induced anticoagulation effect. The ACT for Sonoclot Signature 20 is the time when the clot begins to form at point 21, which is 125 seconds. Sonoclot Signature 22 results from a typical sample with enough heparin to safely proceed with a CPB procedure. The ACT for Sonoclot Signature 22 is the time when the clot begins to form at point 23, which is 500 seconds. Heparin prolongs the liquid phase, thereby producing a larger ACT result.

Figure 3:
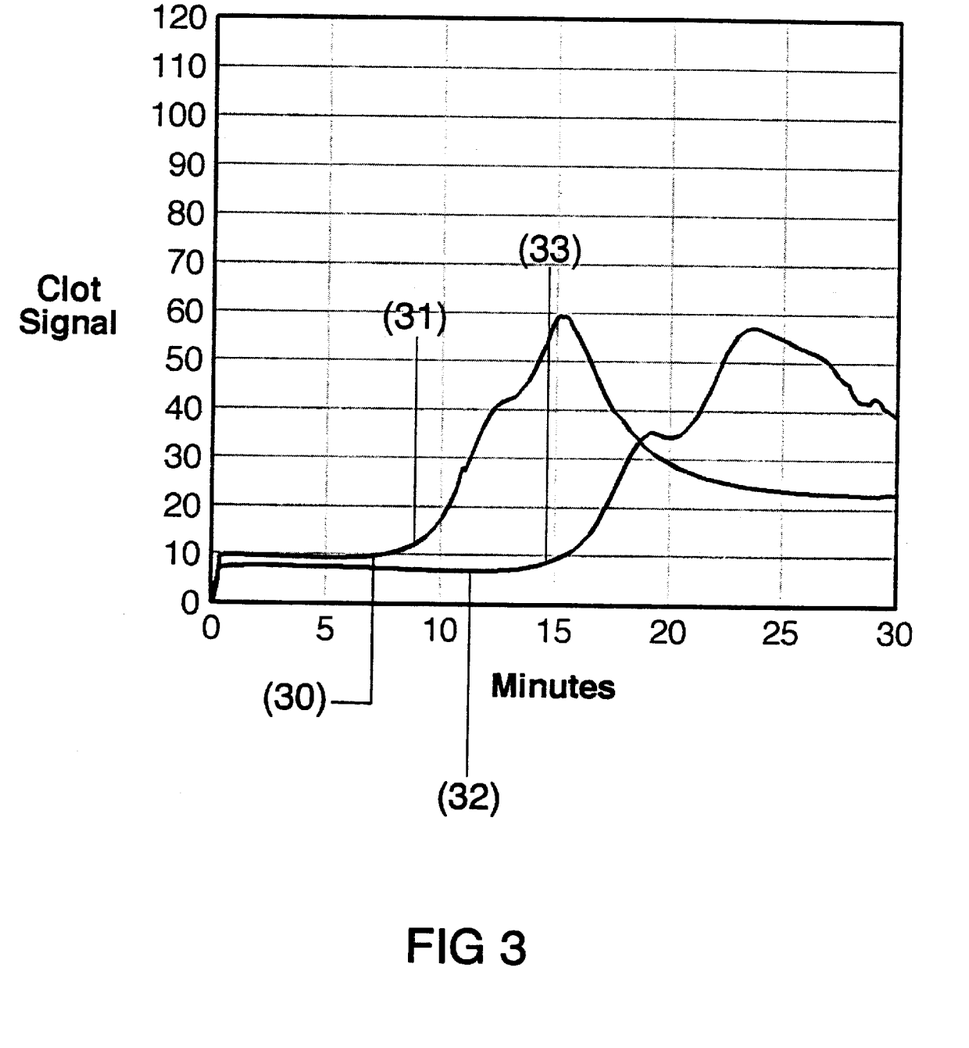
FIG. 3 shows ACT signatures obtained from celite activation run on heparinized whole blood both with and without aprotinin.

FIG. 3 shows how aprotinin affects celite activated ACT results. The blood sample used to generate Sonoclot Signature 30 contains heparin. The ACT result of 480 seconds is found at point 31. The same heparinized blood sample with the addition of aprotinin to produce a level of aprotinin of approximately 300 KIU per mL produced Sonoclot Signature 32. The ACT result of 840 seconds is found at point 33 on Sonoclot Signature 32. The aprotinin altered the ACT result by dramatically extending the result from 480 to 840 seconds. One aspect of the present invention is to reduce the affect of aprotinin on the ACT result.

A preferred sample formulation in accordance with the present invention was developed using an iterative trial and error methodology. Different formulations were evaluated by comparing the ACT result for a heparinized blood sample with the ACT result for equivalent blood sample with the addition of a controlled amount of aprotinin. To generate quantitative numbers for comparing different formulations, the following relationship was used:

$$\text{Aprotin in Sensitivity} = 100\left(\frac{ACT_{(heparin\ and\ aprotinin)} - ACT_{(heparin)}}{ACT_{(heparin)}}\right).$$

The quantity of aprotinin used was 36 µL aprotinin stock (Trasylol®, Bayer Corporation, part number NDC 0026-8197-63) per 1 mL whole blood. This amount of aprotinin is slightly higher than would typically be encountered using a high dose aprotinin management protocol. The Aprotinin Sensitivity was found to vary significantly among different subjects, so the evaluation of the Aprotinin Sensitivity index requires statistical analysis from multiple blood samples.

The quality of a candidate ACT formulation is dependent on two statistical characteristics of the Aprotinin Sensitivity result. First, the mean value of Aprotinin Sensitivity should be near 0%, which indicates that the ACT formulation produces little bias in the presence of aprotinin. Second, the range of the Aprotinin Sensitivity should be small, which indicates that the formulation produces consistent results for all samples. The variance or standard deviation could also be used in this analysis but is not recommended because the distribution function for Aprotinin Sensitivity across a patient population appears likely to be bimodal and not follow a normal distribution.

As a benchmark for Aprotinin Sensitivity performance, the present inventors measured the performance of celite, USP grade kaolin, part number 5645 from Mallinckrodt Chemical, Inc (Kaolin #1), and a kaolin that performs similarly to the kaolin in the kaolin ACT test manufactured by International Technidyne Corporation (Kaolin #2). These results are summarized in Table 1 below.

TABLE 1

| Aprotinin Sensitivity | Average | Range |
| --- | --- | --- |
| Celite | 119% | 81% to 333% |
| Kaolin #1 | 113% | 56% to 182% |
| Kaolin #2 | 34% | −7% to 210% |

The results in Table 1 confirm that current ACT formulations are substantially affected by aprotinin. For celite and Kaolin #1, the average Aprotinin Sensitivity of slightly over 100% confirms that the ACT result is substantially prolonged by aprotinin. For Kaolin #2, the average Aprotinin Sensitivity is 34%, indicating that average ACT results are less affected by aprotinin. However, with Kaolin #2, the range of the Aproinin Sensitivity is very large. In some samples the presence of aprotinin had no significant affect (Aprotinin Sensitivity =−7%) and in other samples the ACT result is extended over 300% by the presence of aprotinin (Aprotinin Sensitivity >200%). None of these formulations provide Aprotinin Sensitivity results that meet the present design expectations for a safe and effective ACT for heparinized blood samples that also contain aprotinin. A formulation that achieved a mean Aprotinin Sensitivity close to 0% and had a small range of Aprotinin Sensitivity results was sought.

The present inventors' search for a preferred formulation began with an investigation of kaolin. This investigation was undertaken because testing showed significantly different aprotinin sensitivity results between USP kaolin from Mallinckrodt and the kaolin activator used by International Technidyne Corporation. Twenty different samples of kaolin were collected with the idea that there may be some variability of performance based on the source of the kaolin. Out of these twenty, only two kaolin samples showed reduced aprotinin sensitivity similar to International Technodyne's kaolin ACT test.

Figure 4A:
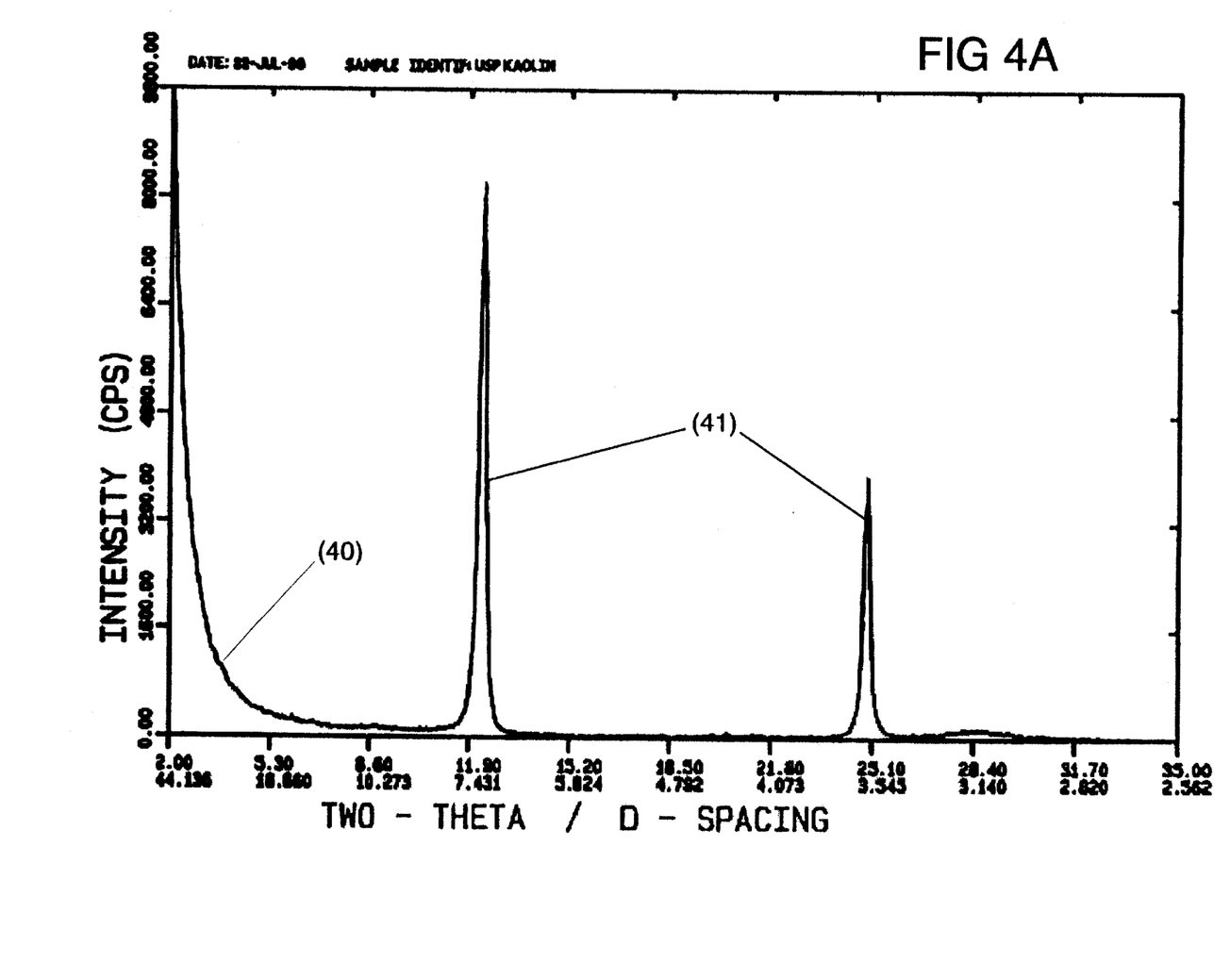
FIG. 4A shows an x-ray diffraction graph for pure kaolin.
Figure 4B:
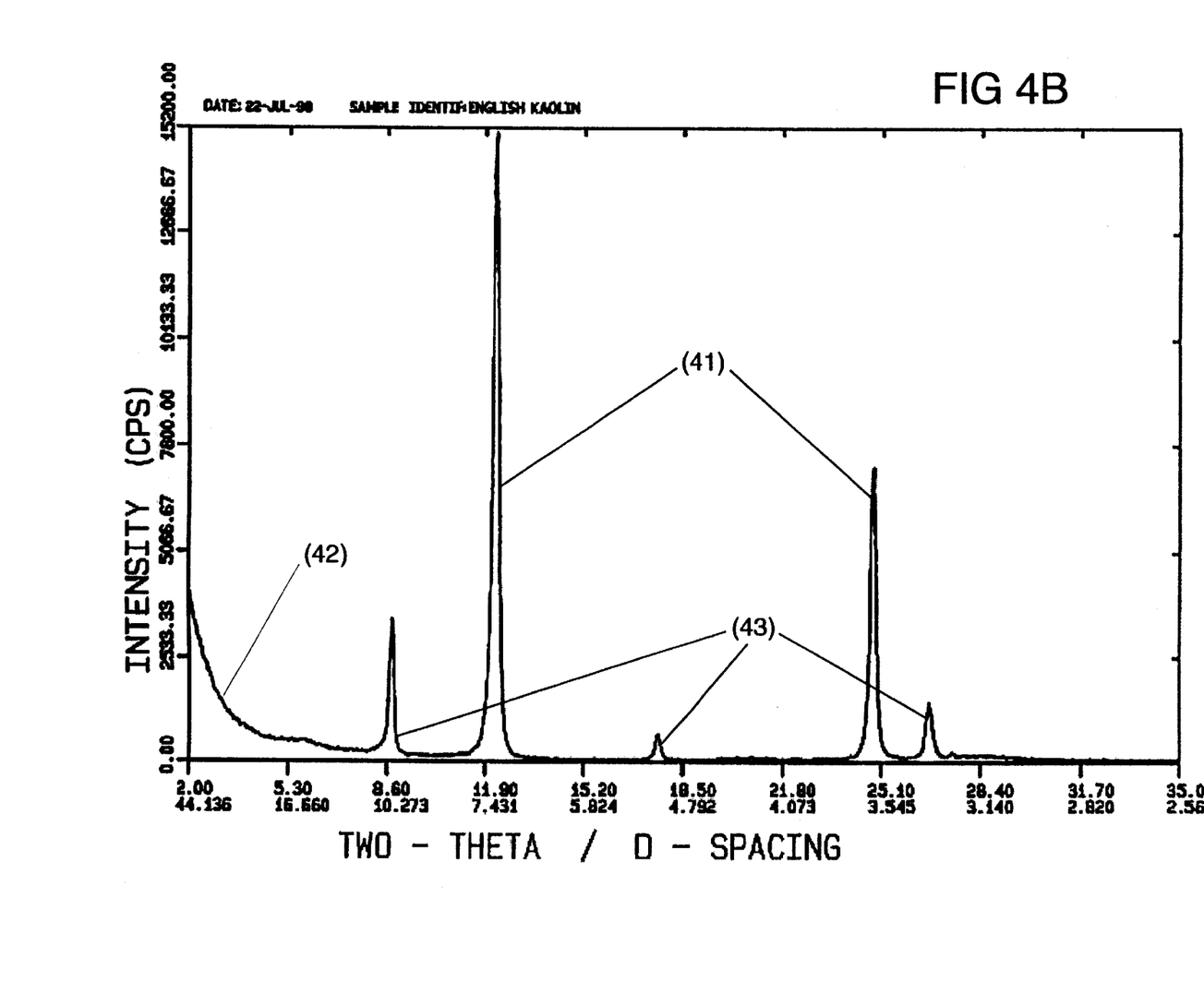
FIG. 4B shows an x-ray diffraction graph for kaolin with natural illite impurity.
Figure 4C:
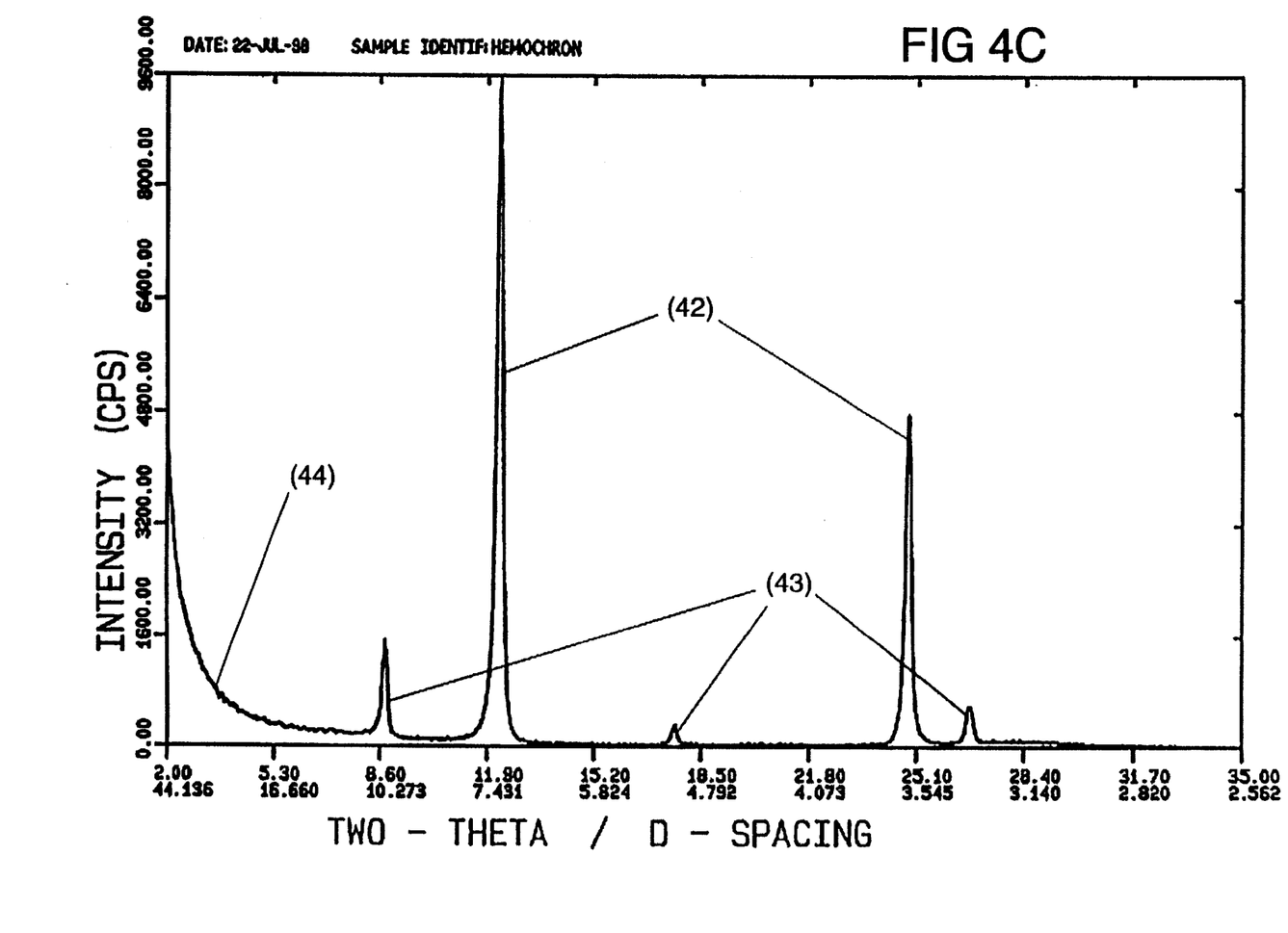
FIG. 4C shows an x-ray diffraction graph for kaolin employed in a prior art ACT test.

To investigate the possible cause for the wide range of activation characteristics among the kaolin samples, the kaolin samples were investigated for impurities. All twenty kaolin samples were analyzed, including the kaolin from International Technidyne, using an x-ray diffraction technique, which determines the composition of a clay by looking at refraction through the crystalline structure. X-ray diffraction analysis was performed with a Siemens Diffrac 5000 at the U.S. Geological Survey, Boulder, Colo. Results were recorded as a refraction pattern as illustrated in the graphs of FIGS. 4A–C. In these graphs, different minerals produce different characteristic graphs. Graph 40 in FIG. 4A is from the Mallinckrodt kaolin that produced ACTs that were significantly prolonged by aprotinin in the presence of heparin. This graph has the characteristic peaks 41 identified with pure kaolin. Graph 42 in FIG. 4B is the refraction pattern from a kaolin sample that produced ACTs that were less affected by aprotinin and performed similarly to the kaolin used in the kaolin ACT manufactured by International Technodyne Corporation. Graph 42 has the characteristic peaks 41 of pure kaolin and contains additional smaller peaks 43 that are characteristic of an illite impurity in the kaolin. Illite is a type of clay with a different mineral composition than kaolin.

Graph 44 in FIG. 4C is the refraction pattern for the kaolin used in the kaolin ACT manufactured by International Technidyne. This graph has the pattern of kaolin peaks 42 with illite impurity peaks 43. A refraction pattern was also generated for kaolin from J. T. Baker Co., Phillipsburg, N.J. The refraction pattern for the Baker kaolin is not included because it was found to be almost identical to the refraction pattern for the other kaolin clays that contained illite impurity. Both kaolin samples with the illite impurity performed approximately equivalent to the kaolin used by International Technidyne. The previously discussed research by Wang that showed average kaolin performance to be substantially unaffected by aprotinin also used kaolin from J. T. Baker Co. This research likely used kaolin that contained illite impurity.

The present inventors' ACT results using kaolin with illite impurities did achieve average performance that was substantially unaffected by aprotinin in heparinized samples. However, it was also found that some blood samples from subjects were significantly affected by aprotinin in the presence of heparin. ACT tests results using kaolin with illite impurities appears to have a bimodal statistical distribution function; most samples are unaffected by aprotinin and others can be strongly affected by aprotinin. Conventional statistical methods that apply to normal distribution functions often do not apply to bimodal distribution functions.

Figure 5:
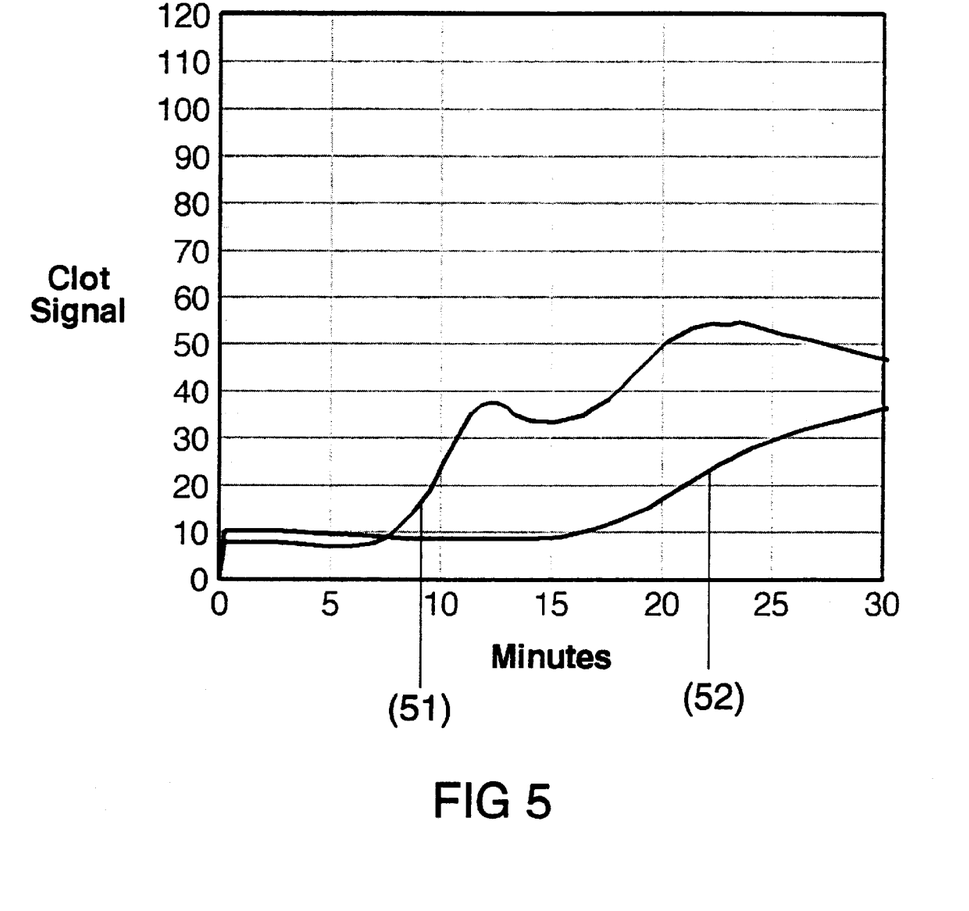
FIG. 5 shows ACT signatures obtained from the use of kaolin with natural illite activation run on heparinized whole blood both with and without aprotinin.

FIG. 5 illustrates one blood sample that was tested with kaolin containing a natural illite impurity that was not stable in the presence of aprotinin. Signature 51 is from a heparinized blood sample using a kaolin that contained illite. Signature 52 is from the same heparinized blood sample and activation formulation except aprotinin was also added. This particular blood sample showed high aprotinin sensitivity for all kaolins tested including kaolin from J. T. Baker Co. and the kaolin in the kaolin ACTs manufactured by International Teledyne. This result indicates that some blood samples produce high aprotinin sensitivities for kaolin containing natural illite impurities.

The present inventors' investigation of these twenty different kaolins may be summarized as follows. Pure kaolin without illite impurity produces ACT results that are substantially prolonged by aprotinin in the presence of heparin, while kaolin with an illite impurity is not prolonged by aprotinin in the presence of heparin for most subjects. However, for some blood samples, kaolin with natural illite impurity still produces ACT results that are substantially prolonged by aprotinin in the presence of heparin.

At this point in the product development process, the present inventors knew enough to develop an ACT test that would perform substantially equivalent to the kaolin ACT manufactured by International Technidyne. This was the original objective of the development project. However, it had also been discovered that the performance of kaolin ACTs using kaolins that were least affected by aprotinin still produced inaccurate results as an indicator of heparin anticoagulant effect in the presence of aprotinin for some patients. Since a prolonged ACT may pose a safety risk for inadequate heparinization, it was decided to investigate developing an ACT formulation that was less affected by aprotinin than current kaolin ACTs.

The present inventors next investigated the effectiveness of illite as an activator. Several different illites from different sources were tested. Illite's performance as an activator for ACT tests was found to be dependent on the source of the clay. However, all illite samples tested produced unacceptable ACT results; clots formed using only illite as an activator were weak, and results were dissimilar from current ACT tests. Illite alone was rejected as an activation formulation.

Adding additional illite to either pure kaolin or the combination of kaolin and natural illite was tested. These formulations provided some reduction in sensitivity to aprotinin. However, in the kaolin plus illite tests, some patients still showed a delay in the presence of both heparin and aprotinin in comparison to heparin alone. Also tested was illite in different combinations with celite, kaolin, and other clay minerals. No illite formulation was found that substantially improved ACT performance of heparinized samples in the presence of aprotinin.

After studying illite, it was recognized that different clay structures exhibited different activation characteristics and different sensitivities to aprotinin in the presence of heparin. Therefore, the present inventors decided to expand their investigation to include several different clay minerals that have similar physical characteristics and chemical compositions, but that differ from each other in subtle structural and chemical aspects. Shale, dickite, rectorite, illite, kaolin, bentonite, and montmorillonite were all investigated. Each of these materials has a different ion exchange capacity and different water absorption characteristics. Of these minerals, bentonite has the greatest ion exchange capacity. Also, bentonite ACT results on heparinized blood were found to be substantially unaffected by aprotinin.

Figure 6:
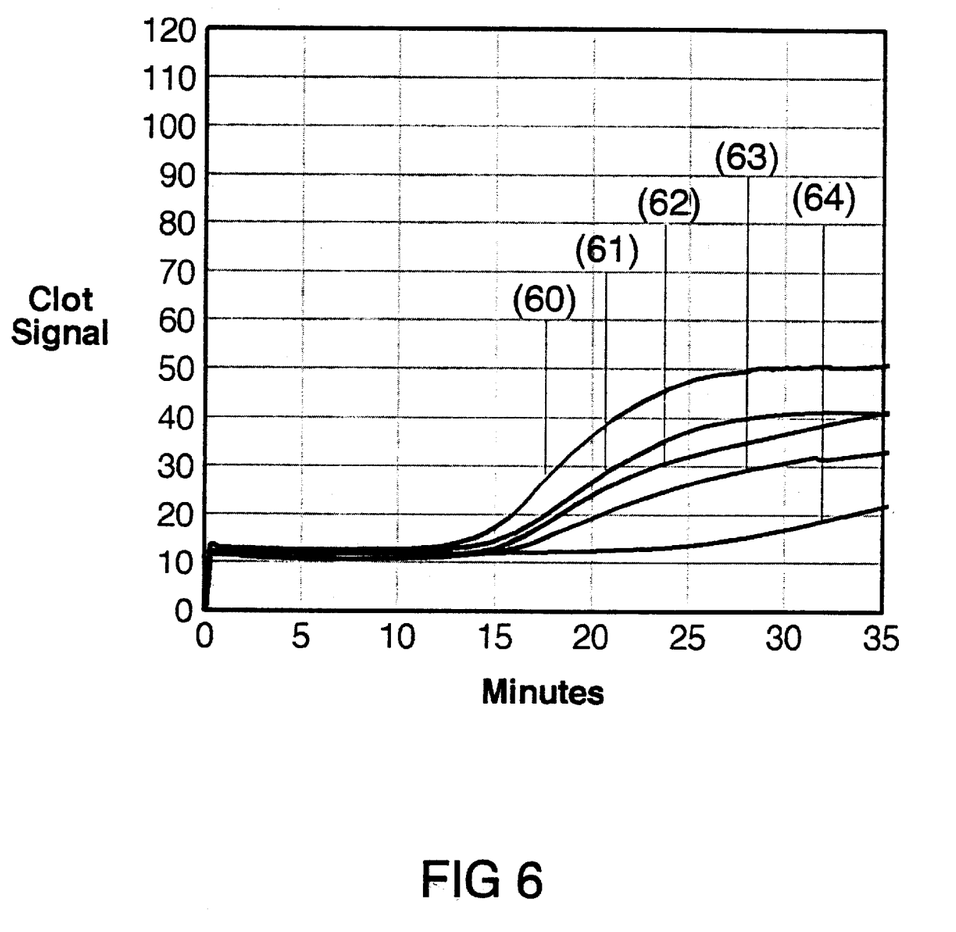
FIG. 6 shows ACT signatures obtained from the use of bentonite activation run on heparinized whole blood.

The present inventors investigated varying the amount of bentonite to produce ACTs that matched ACTs produced with Sienco's celite ACT (part number 800-0432). Typical results are illustrated in FIG. 6. Signature 60 was run on a heparinized blood sample using Sienco's celite ACT test. Signature 61 used 1.2 mg bentonite and produced the shortest bentonite activated ACT result. Signature 64 used less bentonite, 0.04 mg, and produced a very prolonged ACT. Signature 62 used 1.6 mg bentonite and was also longer than signature 61. Signature 63 used 2.0 mg bentonite and produced a slower signature than signatures 61 or 62. From these results, it was learned that it is not possible to adjust the quantity of bentonite to achieve ACT results that can match the activation performance of celite, and that activation time does not always follow a linear relationship with the quantity of activator.

Figure 7:
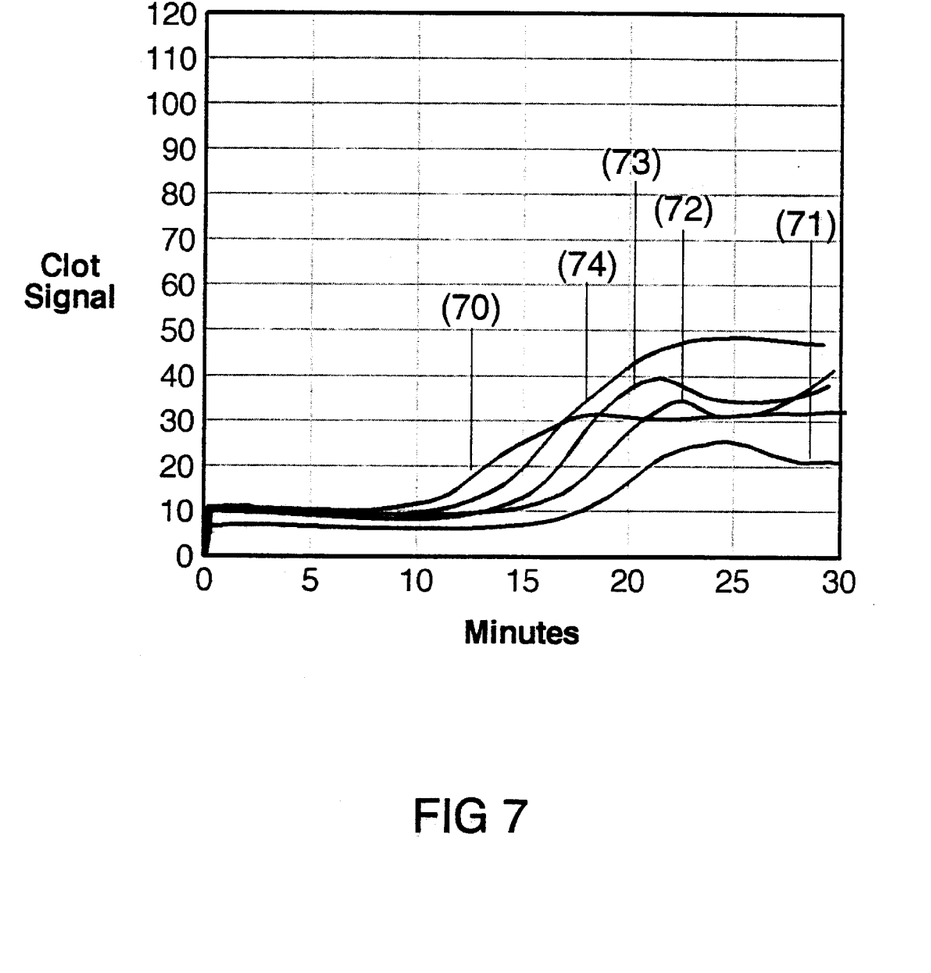
FIG. 7 shows ACT signatures obtained from the use of celite and shale activation run on heparinized whole blood with aprotinin.

After testing numerous formulations and performing many hundreds of tests, the present inventors found that different combinations of clay materials can provide ACT test results that are both sensitive to the quantity of heparin and insensitive to the presence of aprotinin. It was also discovered that by varying the concentrations of selected activators, the aprotinin sensitivity for the ACT formulation could be substantially eliminated. For example, FIG. 7 shows the reduction in aprotinin sensitivity when shale is added to a celite ACT. In the signatures run in FIG. 7, 2 mg of celite was used for each test, while the amount of a shale additive was varied among the individual tests. Signature 70 is a celite control without any shale that was run on a heparinized blood sample. Signatures 71, 72, 73, and 74 were run using the same amount of celite as signature 70 and also contained aprotinin. Signatures 71, 72, 73, and 74 also contained increasing quantities of shale ranging from 0.08 mg, 0.16 mg, 0.24 mg, to 0.32 mg shale, respectively. These signatures illustrate that shale has a dose dependent neutralizing effect on aprotinin. At the highest tested level of shale in FIG. 7, signature 74 approached the celite response in signature 70.

At this point in the investigation, it was believed that with careful selection of materials a formulation could likely be identified that simultaneously produced a predetermined heparin dose response and achieved low aprotinin sensitivity. For compatibility with current products, the present inventors determined that the desired target ACT heparin dose response should match the current heparin dose response of Sienco's celite ACT (part number 800-0432). Consequently, celite was considered as a preferred material to provide contact activation for the formulation. Bentonite was considered as a preferred additive for the activation formulation to reduce aprotinin sensitivity, although other materials also showed good potential.

After additional testing, the selected preferred formulation was chosen to be 3.75 mg of bentonite from Charles B. Chrystal Co, Inc., New York, N.Y., and 3.0 mg of celite 315 from World Minerals, Inc., Santa Barbara, Calif., per 1 mL sample of whole blood. It was observed that this preferred formulation also inhibits the clot retraction phase of the Sonoclot Signature, which is not a design consideration for this test. The individual ACT tests for the preferred formulation were manufactured using a dry fill process. Each material was weighed out individually on an analytical balance and added to each test cuvette. Stir bars were added to the cuvettes, and the cuvettes were then capped with a plastic lid. The individual tests were tapped several times on a hard surface immediately prior to testing to ensure that the activation powder was positioned on the bottom of the cuvette for thorough resuspension in the blood sample. Table 2 below shows the performance of the preferred formulation in comparison to the previously discussed celite and kaolin formulations.

TABLE 2

| Aprotinin Sensitivity | Average | Range |
|---|---|---|
| Celite | 119% | 81% to 333% |
| Kaolin #1 | 113% | 56% to 182% |
| Kaolin #2 | 34% | −7% to 210% |
| Preferred Formulation | −2% | −10% to 8% |

The mean Aprotinin Sensitivity for the preferred formulation was 2%, which is statistically equivalent to a perfect mean of 0%. The range of Aprotinin Sensitivity results was −10% to 8%. This range is comparable to normal statistical variation for an ACT test run in duplicate. This performance is statistically equivalent to the ideal performance goal for an ACT that is insensitive to aprotinin. Alternative formulations may vary the quantity or types of materials used for activation or reduction of aprotinin sensitivity.

Figure 8:
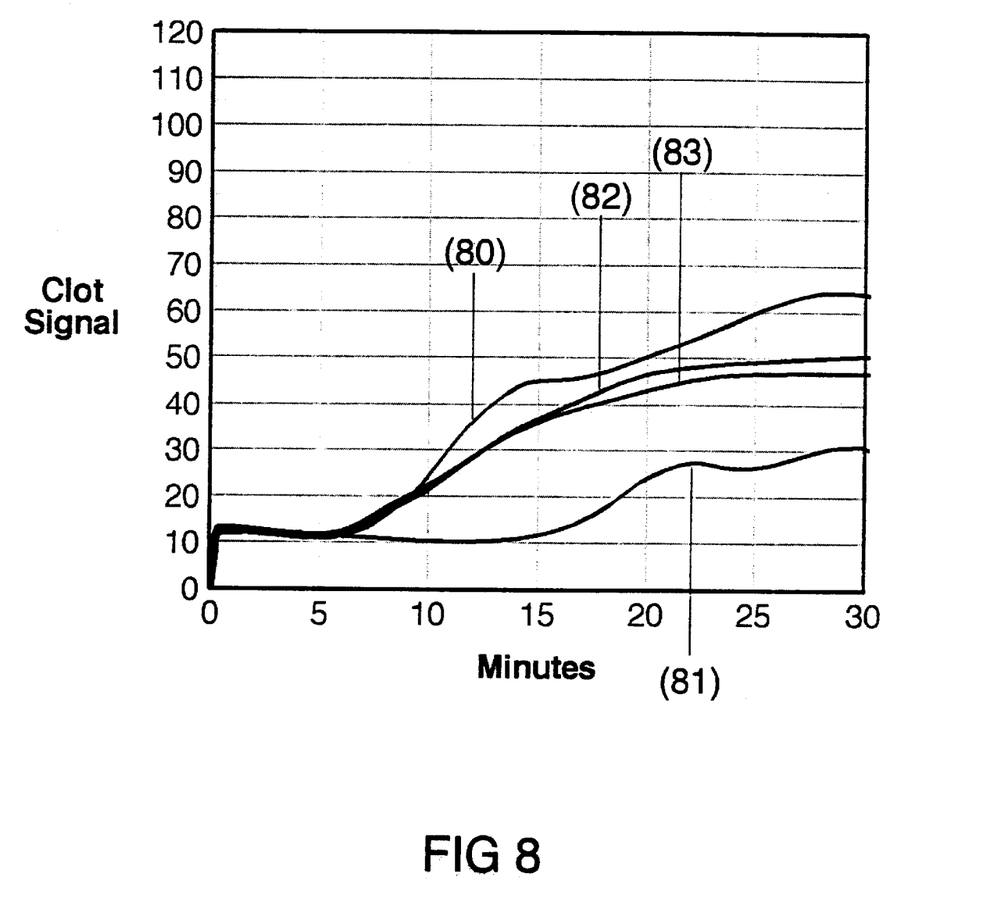
FIG. 8 shows ACT signatures obtained from the use of either celite or celite and bentonite activation run on heparinized whole blood both with and without aprotinin.

FIG. 8 illustrates the performance of the preferred formulation on a heparinized blood sample. Signatures 80 and 81 are controls using Sienco's celite activated ACT. Signature 81 also contains aprotinin and shows the typical prolonged ACT associated with celite ACT tests on heparinized blood in the presence of aprotinin. Signatures 82 and 83 use the preferred activation formulation. Signature 82 is without aprotinin. Signature 83 is with aprotinin. The performance of signatures 80, 82, and 83 are substantially equivalent for purposes of ACT testing. This example shows that the design objectives for activation and aprotinin sensitivity have both been achieved for this blood sample. Testing also showed a reduction in aprotinin sensitivity for blood samples taken from individuals that have large aprotinin sensitivities to kaolin ACTs with natural illite impurities. A detailed statistical study of larger patient populations is necessary for a more complete assessment of actual aprotinin sensitivity performance for clinical patient populations.

We claim:

1. An in vitro diagnostic process for measuring blood coagulation, the process comprising the steps of:
   providing a test container for holding a blood sample, wherein said blood sample contains heparin and aprotinin therein;
   adding a reagent for contact activation to said blood sample, the reagent containing a contact activator selected from the group of clay minerals consisting of bentonite, illite, shale, montmorillonite, rectorite, and dickite, and measuring the coagulation of the blood sample, wherein said reagent serves to reduce the sensitivity and variability of the process to aprotinin in said heparinized blood sample.

2. An in vitro diagnostic process for measuring blood coagulation, the process comprising the steps of:
   providing a test container for holding a blood sample, wherein said blood sample contains heparin and aprotinin therein;

adding said blood sample to said test container;

adding one or more additive reagents for contact activation to said blood sample;

adding a further additive reagent to said blood sample and measuring the coagulation of the blood sample, wherein said further additive reagent serves to reduce the sensitivity and variability of the process to aprotinin in said heparinized blood sample.

3. A process as in claim 2, wherein said one or more additive reagents are selected from the group consisting of celite, glass beads, and clay minerals.

4. A process as in claim 3, wherein said clay minerals comprise illite, bentonite, kaolin, shale, montmorillonite, rectorite, and dickite.

5. A process as in claim 2, wherein said one or more additive reagents are selected from the group consisting of celite, glass beads, illite, bentonite, kaolin, shale, montmorillonite, rectorite, and dickite.

6. A process as in claim 2, wherein said further additive reagent is selected from the group consisting of illite, bentonite, kaolin, shale, montmorillonite, rectorite, and dickite.

7. A method for characterizing the undesired affect of aprotinin on an activated clotting time in vitro diagnostic test, the method comprising the steps of:

(a) performing an activated clotting time test on a sample of blood containing heparin;

(b) performing an activated clotting time test on a sample of blood containing both heparin and aprotinin; and (c) computing a quantified sensitivity of the activated clotting time to the aprotinin from the results of the tests performed in previous steps (a) and (b).

8. A method as in claim 7, wherein said quantified sensitivity is computed by subtracting a result of the test of step (a) from a result of the test of step (b), dividing the difference obtained by the result of the test of step (a) to obtain a quotient, and multiplying the quotient by 100.

9. A method as in claim 7, wherein the sample of blood employed in the activated clotting time test of step (a) contains a quantity of heparin sufficient to prolong the activated clotting time to beyond 300 seconds.

10. A method as in claim 7, wherein the samples of blood employed in the activated clotting time tests of steps (a) and (b) contain equal amounts of heparin.

11. A method as in claim 7, wherein the activated clotting time tests of steps (a) and (b) are repeatedly performed, using samples of blood from multiple donors, to thereby generate statistical data relating to the sensitivity of the activated clotting time to aprotinin for a population sample.

* * * * *